United States Patent [19]
Buchanan et al.

[11] Patent Number: 5,763,720
[45] Date of Patent: Jun. 9, 1998

[54] TRANSALKYLATION PROCESS FOR PRODUCING AROMATIC PRODUCT USING A TREATED ZEOLITE CATALYST

[75] Inventors: John S. Buchanan, Hamilton; Arthur W. Chester, Cherry Hill, both of N.J.; Anthony S. Fung, Wilmington, Del.; Timothy F. Kinn, Deptford; Sadi Mizrahi, Cherry Hill, both of N.J.

[73] Assignee: Mobil Oil Corporation, Fairfax, Va.

[21] Appl. No.: 937,280

[22] Filed: Sep. 15, 1997

Related U.S. Application Data

[63] Continuation of Ser. No. 386,892, Feb. 10, 1995, abandoned.

[51] Int. Cl.$^6$ .................................................. C07C 6/12
[52] U.S. Cl. .................................................. 585/475; 585/906
[58] Field of Search .................................. 585/475, 470, 585/474, 906

[56] References Cited

U.S. PATENT DOCUMENTS

| | | | |
|---|---|---|---|
| 3,729,409 | 4/1973 | Chen | 208/135 |
| 3,767,568 | 10/1973 | Chen | 208/134 |
| 3,832,449 | 8/1974 | Rosinski et al. | 423/328 |
| 3,948,758 | 4/1976 | Bonacci et al. | 208/92 |
| 3,957,621 | 5/1976 | Bonacci et al. | 208/60 |
| 3,965,208 | 6/1976 | Butter et al. | 260/671 M |
| 3,965,209 | 6/1976 | Butter et al. | 260/671 M |
| 4,001,346 | 1/1977 | Chu | 260/671 M |
| 4,007,231 | 2/1977 | Butter | 260/672 T |
| 4,011,276 | 3/1977 | Chu | 260/672 T |
| 4,016,218 | 4/1977 | Haag et al. | 260/671 R |
| 4,016,219 | 4/1977 | Kaeding | 260/672 T |
| 4,029,716 | 6/1977 | Kaeding | 260/672 T |
| 4,052,476 | 10/1977 | Morrison | 260/672 T |
| 4,100,215 | 7/1978 | Chen | 260/671 M |
| 4,117,026 | 9/1978 | Haag et al. | 260/671 R |
| 4,127,471 | 11/1978 | Suggitt et al. | 208/60 |
| 4,150,062 | 4/1979 | Garwood et al. | 260/673 |
| 4,152,364 | 5/1979 | Chu | 585/454 |
| 4,172,813 | 10/1979 | Feinstein et al. | 585/475 |
| 4,341,914 | 7/1982 | Berger | 585/474 |
| 4,365,104 | 12/1982 | Kaeding | 585/467 |
| 4,367,359 | 1/1983 | Kaeding | 585/467 |
| 4,370,508 | 1/1983 | Kaeding | 585/467 |
| 4,380,685 | 4/1983 | Chu | 585/466 |
| 4,418,235 | 11/1983 | Haag et al. | 585/407 |
| 4,753,720 | 6/1988 | Morrison | 208/135 |
| 4,812,223 | 3/1989 | Hickey, Jr. et al. | 208/111 |
| 4,857,666 | 8/1989 | Barger et al. | 585/323 |
| 4,891,458 | 1/1990 | Innes et al. | 585/323 |
| 4,983,274 | 1/1991 | Chen et al. | 208/111 |
| 5,030,787 | 7/1991 | Absil et al. | 585/475 |
| 5,406,016 | 4/1995 | Cook et al. | 585/475 |

OTHER PUBLICATIONS

Das et al., "Transalkylation and Disproportionation of Toluene and $C_9$ Aromatics over Zeolite Beta" 23 Catalyst Letters pp. 161–168 (1994).

Das et al., "Zeolite Beta Catalyzed $C_7$ and $C_9$ Aromatics Transformation" 116 Applied Catalysis A: General, pp. 71–79 (1994).

Wang et al., "Disproprtionation of Toluene and of Trimethylbenzene and Their Translkylation over Zeolite Beta", 29 Ind. Eng. Chem. Res. pp. 2005–2012 (1990).

Yamada et al. "Hydrogenation by $CoMo/Al_2O_3$ Catalyst (Part 3) Effect of $H_2S$ on Hydrogenation of Monoaromatic Hydrocarbons" vol. 31, No. 2, Sekiyu Gakkaishi, pp. 118–124 (1988).

*Primary Examiner*—Glenn Caldarola
*Assistant Examiner*—Thuan D. Dang
*Attorney, Agent, or Firm*—Blossom E. Loo; Dennis P. Santini

[57] ABSTRACT

A heavy aromatics feed is converted to lighter aromatics products, such as benzene, toluene and xylenes by contacting a $C_9+$ aromatics fraction and benzene and/or toluene over a catalyst comprising a zeolite, such as ZSM-12, and a hydrogenation component, preferably platinum. The catalyst, complete with hydrogenation component, is treated to reduce aromatics loss. Treatment includes exposure to steam and/or sulfur after incorporation of the hydrogenation component. For additional stability and aromatics retention the steamed and/or sulfur treated catalyst is sulfided by cofeeding a source of sulfur. In a further embodiment of the invention a low hydrogen partial pressure is employed to retain aromatics.

31 Claims, 3 Drawing Sheets

TRANSALKYLATION PROCESS FOR PRODUCING AROMATIC PRODUCT USING A TREATED ZEOLITE CATALYST

This application is a continuation of application Ser. No. 08/386,892, filed Feb. 10, 1995, now abandoned.

FIELD OF THE INVENTION

The invention relates to the production of xylenes from a feedstock comprising benzene and/or toluene and heavy aromatics, specifically, $C_9+$ aromatics. More specifically, the invention relates to the production of xylenes over a catalyst comprising a zeolite and a hydrogenation component.

BACKGROUND OF THE INVENTION

Para-xylene is an important by-product of petroleum refining because it is used in significant quantities for the manufacture of terephthalic acid which is reacted with polyols such as ethylene glycol in the manufacture of polyesters.

The major source of para-xylene is catalytic reformate which is prepared by mixing petroleum naphtha with hydrogen and contacting the mixture with a strong hydrogenation/ dehydrogenation catalyst such as platinum on a moderately acidic support such as a halogen treated alumina.

Usually, a $C_6$ to $C_8$ fraction is separated from the reformate, extracted with a solvent selective for aromatics or aliphatics to separate these two kinds of compounds and produce a mixture of aromatic compounds which is relatively free of aliphatics. This mixture of aromatic compounds usually contains benzene, toluene and xylenes (BTX) along with ethyl benzene.

Liquids from extremely severe thermal cracking, e.g. high temperature steam cracking of naphtha are also rich in aromatics and may be used to prepare BTX in a similar manner.

Concentrated aromatic fractions are also provided by severe cracking over such catalysts as ZSM-5 and by conversion of methanol over ZSM-5.

Refineries have focused on the production of xylenes by transalkylation of $C_9+$ aromatics, which would normally only be of value as fuel, and toluene, over zeolite containing catalysts. The stability and transalkylation selectivity of zeolite beta for this reaction is the subject of several recent publications. See Das et al. "Transalkylation and Disproportionation of Toluene and $C_9$ Aromatics over Zeolite Beta" 23 Catalyst Letters pp. 161–168 (1994); Das et al. "Zeolite Beta Catalyzed $C_7$ and $C_9$ Aromatics Transformation" 116 Applied Catalysis A: General, pp. 71–79 (1994) and Wang et al. "Disproportionation of Toluene and of Trimethylbenzene and Their Transalkylation over Zeolite Beta", 29 Ind. Eng. Chem. Res. pages 2005–2012 (1990).

Additionally, processes for producing xylenes from hydrocarbon fractions containing substituted aromatics have been disclosed in the patent literature. U.S. Pat. No. 4,380, 685 discloses the para-selective alkylation, transalkylation or disproportionation of a substituted aromatic compound to provide a mixture of dialkylbenzene compounds employing as a catalyst a zeolite characterized by a Constraint Index of 1 to 12 and a silica/alumina mole ratio of at least 12/1, the catalyst having incorporated thereon various metals and phosphorus.

Various techniques for enhancing the para-selectivity of zeolite catalysts employed in the production of xylenes have been described. Specific Para-selectivity enhancing techniques which have been described include treatment with a sulfur compound in U.S. Pat. No. 4,365,104; treatment with carbon dioxide in U.S. Pat. No. 4,367,359; treatment with a nitrogen compound in U.S. Pat. No. 4,370,508; treatment with a group VA element in U.S. Pat. No. 3,965,208; treatment with steam in U.S. Pat. No. 3,965,209; treatment by deposition of coke in U.S. Pat. No. 4,001,346; treatment with a boron compound in U.S. Pat. No. 4,100,215; and treatment with ammonium hydrogen phosphate in U.S. Pat. No. 4,152,364. Toluene is shown to be disproportionated in U.S. Pat. Nos. 4,052,476; 4,007,231; 4,011,276; 4,016,219 and 4,029,716.

During the dealkylation reactions that, typically, accompany the conversion of substituted aromatics to xylenes, olefins are formed which tend to undergo secondary reactions resulting in the formation of coke which rapidly deactivates the catalyst. These olefins also tend to take part in the formation of heavy aromatic compounds which are undesirable refinery by-products and which can also contribute to catalyst deactivation.

One approach for solving the problems posed by the olefins formed during the dealkylation reactions which accompany xylene production has been to encourage olefin hydrogenation. Hydrogenation metals, such as platinum, are known for their ability to hydrogenate olefins and prevent coke formation and have been incorporated into the catalysts. Hydrogenation metals are also employed to facilitate dealkylation.

U.S. Pat. No. 5,030,787 discloses an improved process for the vapor-phase conversion of a feedstock containing at least one $C_9+$ aromatic compound to a product containing substantial quantities of $C_6$ to $C_8$ compounds, e.g. benzene and xylenes. The conversion occurs over a catalyst which contains a zeolite possessing a Constraint Index of from 1 to about 3, e.g. zeolites MCM-22, ZSM-12 and zeolite beta. Steam treatment of the zeolite is proposed, see Col. 9, lines 66–67. A Group VIII metal can be included with the catalyst. In the specific examples of the disclosure the zeolite is subjected to the steam treatment prior to incorporation of the hydrogenation metal, see Examples 20–22.

U.S. Pat. No. 4,418,235 also discloses increasing the catalytic activity of a zeolite used for transalkylation by steam treatment and suggests incorporating a Group VIII metal into the zeolite.

U.S. Pat. No. 3,965,209 discloses the production of paraxylene by methylation of toluene in the presence of a zeolite which has been steamed to reduce its alpha value. Incorporation of a metal into the zeolite by replacing the original alkali metal of the zeolite with a Group VIII metal is disclosed.

U.S. Pat. No. 3,948,758 discloses preparing xylenes by hydrocracking an alkyl aromatics-rich and aliphatics-lean hydrocarbon fraction and toluene as a cofeed over a zeolite catalyst with a hydrogenation/dehydrogenation component, such as a Group VIII metal. The alkyl aromatics of the feed, to some extent, are rearranged by disproportionation and transalkylation. It is disclosed that because at lower temperatures which are necessary for high conversions without excessive dealkylation, the thermodynamic equilibrium tends to increase hydrogenation of the aromatic ring so nickel, a less active hydrogenation component, as compared to platinum, is preferred.

U.S. Pat. No. 4,857,666 discloses transalkylating an aromatic feed over mordenite and suggests modifying the zeolite by steam deactivation or incorporating a metal modifier into the catalyst.

Employing high hydrogen partial pressures or high hydrogen to hydrocarbon mole ratios have been considered for purposes of minimizing catalyst aging. However, the hydrogenation component and high hydrogen partial pressures promote saturation of the aromatic compounds resulting in low yields of the desirable lighter aromatics products such as benzene, toluene and xylenes. Also, maintaining a high hydrogen to hydrocarbon mole ratio requires large reactors which are costly to manufacture and maintain.

SUMMARY OF THE INVENTION

This invention reduces the problems caused by olefins which are formed during the production of xylenes from substituted aromatics by providing a catalyst that saturates olefins formed during the process while minimizing saturation of aromatics. The invention also avoids the need for the high hydrogen partial pressures and high hydrogen to hydrocarbon mole ratios thought necessary to minimize catalyst aging.

The invention relates to a process for the conversion of a feedstock containing $C_9+$ aromatic compounds to a product comprising light aromatic products and xylenes. More specifically, the invention is a process for converting a feedstock containing $C_9+$ aromatic hydrocarbons to light aromatic products and xylenes comprising the step of:

contacting the $C_9+$ aromatic hydrocarbons and a feedstock comprising benzene and/or toluene with a catalyst composition, the catalyst composition comprising a zeolite and a hydrogenation functionality, the zeolite has a constraint index ranging from about 0.5 to 3 under transalkylation reaction conditions to produce a product comprising xylenes. The hydrogenation functionality of the catalyst composition has sufficient olefins saturation activity to avoid rapid catalyst deactivation but has minimum aromatics saturation activity.

An objective of the invention is the conversion of $C_9+$ aromatic hydrocarbons to a product comprising light aromatic products and xylenes, without substantial loss of aromatic hydrocarbons through aromatics saturation.

A feature of the invention is a catalyst of minimum aromatics hydrogenation activity comprising a zeolite and a hydrogenation component. The catalyst is achieved by incorporation of the hydrogenation component into the catalyst followed by treatment to minimize aromatics saturation activity.

A further feature of the invention is a process for subjecting the catalyst to the hydrocarbon conversion process under start-up conditions of low hydrogen partial pressure and/or low hydrogen to hydrocarbon mole ratio.

An advantage of the invention is that a product rich in xylenes is produced by contacting a feedstock comprising $C_9+$ aromatic hydrocarbons and toluene over a catalyst having characteristics which enable it to convert the $C_9+$ aromatic hydrocarbons with a minimum of aromatics saturation and catalyst aging.

The invention alleviates the problems of catalyst aging and heavy aromatics formation posed by olefins formed during the conversion of heavy aromatics and toluene over catalysts comprising a zeolite and a hydrogenation component. The invention also solves the problem of high hydrogen partial pressures to avoid catalyst aging by providing a more stable catalyst which permits lower hydrogen partial pressures to be employed.

The invention is directed to a process for converting a feedstock comprising $C_9+$ aromatic hydrocarbons to lighter aromatic products comprising the step of:

contacting a feed comprising the $C_9+$ aromatic hydrocarbons, benzene and/or toluene under transalkylation reaction conditions with a catalyst composition comprising a zeolite having a Constraint Index ranging from about 0.5 to about 3 and a hydrogenation functionality to produce a product comprising xylenes, the catalyst composition having a hydrogenation functionality which is treated to substantially minimize loss of aromatics as determined by comparing the aromatics content of the feed with the aromatics content of the product.

The invention is also directed to a process for converting a feedstock containing benzene and/or toluene and $C_9+$ aromatic hydrocarbons to a product comprising xylenes comprising the steps of:

treating a catalyst composition comprising a zeolite and a hydrogenation component with steam and/or a source of sulfur, the zeolite having a constraint index ranging from about 0.5 to 3;

contacting the treated catalyst with the feedstock in the presence of hydrogen under transalkylation reaction conditions to produce a product comprising xylenes and which comprise lower than about 10% less than the amount of aromatics in the feedstock.

The invention is also directed to a process for making a catalyst for $C_9+$ aromatics transalkylation comprising the steps of forming a catalyst composite which comprises a zeolite having a Constraint Index ranging from about 0.5 to 3, a hydrogenation component and an inorganic oxide binder followed by the steps of treating the catalyst composite by (1) exposing the catalyst composite to steam and/or a source of sulfur and (2) contacting the catalyst composite with a feedstock comprising $C_9+$ aromatics and benzene and/or toluene under conditions of temperature ranging from about 700° F. to about 950° F. and hydrogen partial pressure of below about 300 psia.

DETAILED DESCRIPTION OF THE INVENTION

The invention relates to a process for converting a feedstock containing $C_9+$ aromatic hydrocarbons and benzene and/or toluene to xylenes and lighter aromatic products comprising the steps of:

contacting the feedstocks with a catalyst composition comprising a zeolite and a hydrogenation component, the zeolite characterized by a constraint index ranging from about 0.5 to 3.

The conversion is conducted in the presence of hydrogen under transalkylation reaction conditions to produce a product comprising xylenes.

The conditions of reaction are sufficient to convert the feedstock to a product containing substantial quantities of $C_6$–$C_8$ aromatic compounds such as benzene, toluene and xylenes, especially xylenes. The product effluent is separated and distilled to remove the desired xylenes product. Any unreacted materials such as toluene and/or $C_9+$ hydrocarbons can be recycled to the transalkylation reaction zone.

The feature of the invention which achieves the production of xylenes without substantial aromatics saturation resides in the use of a zeolite-containing catalyst having a hydrogenation functionality which has been treated to minimize aromatics saturation and to provide stable operation.

Transalkylation Catalyst

The reactions of this invention are catalyzed by contact with a transalkylation catalyst which has been specially prepared in order to accomplish the objectives of the invention.

The Zeolite

As previously mentioned, the transalkylation catalyst comprises a zeolite. Zeolite catalysts which are useful in the process of this invention are those that possess a Constraint Index of from about 0.5 to 3.

The method by which Constraint Index is determined is described fully in U.S. Pat. No. 4,016,218, incorporated herein by reference for details of the method.

Constraint Index (CI) values for some typical zeolites including some which are suitable as catalysts in the process of this invention are set forth in Table A:

TABLE A

| | CI (at test temperatures) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordentite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above described Constraint Index is an important and even critical definition of those zeolites which are useful in the instant invention. The very nature of this parameter and the recited technique by which it is determined, however, admits of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g., temperature, as to establish more than one value for the Constraint Index of a particlar zeolite.

It is to be realized that the above CI values typically characterize the specified zeolites but that such are the cumulative result of several variables useful in the determination and calculation thereof. Thus, for a given zeolite exhibiting a CI value within the range of 3 or less, depending on the temperature employed during the test method within the range of 290° C. to about 538° C., with accompanying conversion between 10% and 60%, the CI may vary within the indicated range of 3 or less. Accordingly, it will be understood to those skilled in the art that the CI as utilized herein, while affording a highly useful means for characterizing the zeolites of interest, is approximate taking into consideration the manner of its determination with the possibility in some instances of compounding variable extremes. However, in all instances, at a temperature within the above-specified range of 290° C. to about 538° C., the CI will have a value for any given zeolite of interest herein of not greater than about 3.

Some zeolite catalysts which are especially useful in the process of this invention include zeolites MCM-22, ZSM-12 and Beta.

ZSM-12 is more particularly described in U.S. Pat. No. 3,832,449, the entire contents of which are incorporated by reference herein.

Zeolite Beta is more particularly described in U.S. Pat. No. Re. 28,341 (of original U.S. Pat. No. 3,308,069), the entire contents of which are incorporated by reference herein.

Zeolite MCM-22, or simply "MCM-22", appears to be related to the composition named "PSH-3" described in U.S. Pat. No. 4,439,409. Zeolite MCM-22 does not appear to contain all the components apparently present in the PS H-3 compositions. Zeolite MCM-22 is not contaminated with other crystal structures, such as ZSM-12 or ZSM-5, and exhibits unusual sorption capacities and unique catalytic utility when compared to the PSH-3compositions synthesized in accordance with U.S. Pat. No. 4,439,409.

Catalyst Binder

It may be desirable to incorporate the selected zeolite catalyst with another material which is resistant to the temperatures and other conditions employed in the process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite catalyst, i.e. combined therewith or present during its synthesis, which itself is catalytically active, may change the conversion and/or selectivity of the catalyst. Inactive materials suitably serve as diluents to control the amount of conversion so that transalkylated products can be obtained economically and orderly without employing other means for controlling the rate of reaction. These materials may be incorporated into naturally occurring clays, e.g. bentonite and kaolin to improve the crush strength of the catalyst under commercial alkylation operating conditions. The materials, i.e. clays, oxides, etc. function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the zeolite catalyst herein include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Binders useful for compositing with zeolite also include inorganic oxides, notably alumina.

In addition to the foregoing materials, the zeolite catalyst can be composited with a porous matrix material such as an inorganic oxide selected from the group consisting of silica, alumina, zirconia, titania, thoria, beryllia, magnesia, and combinations thereof such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 95 percent by weight and more usually, particularly when the composite is prepared in the form of beads, in the range of about 2 to about 80 weight percent of the composite.

The zeolite is usually admixed with the binder or matrix material so that the final composite catalyst contains the binder in amounts ranging from about 5 to about 90 weight percent and preferably from about 10 to about 60 weight percent.

The zeolite catalyst can be shaped into a wide variety of particle sizes. In general, the particles are in the form of a powder, a granule or a molded product such as an extrudate having a particle size sufficient to pass through 2 mesh (Tyler) screen and be retained on a 400 mesh (Tyler) screen. In cases where the catalyst is molded such as by extrusion, the crystals can be extruded before drying or partially dried and then extruded.

Hydrogenation Component

The zeolite is employed in combination with a hydrogenation component such as a metal selected from Group VIII of the Periodic Table of the Elements (CAS version, 1979). Specific examples of useful hydrogenation materials are iron, ruthenium, osmium, nickel, cobalt, rhodium, iridium, or a noble metal such as platinum or palladium.

Suitable platinum compounds for impregnating the catalyst with platinum include chloroplatinic-acid, platinous chloride and various compounds containing platinum amine complex, such as $Pt(NH_3)_4Cl_2 \cdot H_2O$.

The amount of the hydrogenation component is selected according to a balance between hydrogenation activity and catalytic functionality. Less of the hydrogenation component is required when the most active metals such as platinum are used as compared to palladium which does not possess such strong hydrogenation activity. Generally, less than 10 wt. % is used and often not more than 1 wt. %.

The hydrogenation component can be incorporated into the catalyst composition by co-crystallization, exchanged into the composition to the extent a Group IIIA element, e.g., aluminum, is in the structure, impregnated therein or mixed with the zeolite and the inorganic oxide matrix. Such component can be impregnated in, or on, the zeolite such as for example, in the case of platinum, by treating the zeolite with a solution containing a platinum metal-containing ion.

In this regard, the noble metal may be incorporated into the catalyst by conventional techniques such as impregnation or ion exchange (or both) and may use solutions of simple or complex ions of the chosen metal, e.g. complex such as $Pt(NH_3)_4^{2+}$.

Alternatively, a compound of the selected hydrogenation component may be added to the zeolite when it is being composited with a binder or matrix material and after the matrixed catalyst has been formed into particles e.g. by extrusion or pelletizing.

The catalyst may be activated by calcination after drying the particles in order to remove organic components used in the synthesis of the zeolite, after which, ion-exchange may be carried out as well as impregnation.

After treatment with the hydrogenation function, the catalyst composite is usually dried by heating the catalyst at a temperature of about 150° to about 320° F. (about 65° to about 160° C.) for at least about 1 minute and generally not longer than about 24 hours preferably from about 230° F. to about 290° F. (about 110° C. to about 143° C.), at pressures ranging from about 0 to about 15 psia. Thereafter, the catalyst composite is calcined in a stream of dry gas, such as air or nitrogen at temperatures of from about 500° F. to about 1200° F. (about 260° C. to about 649° C.) for about 1 to about 20 hours. Calcination is preferably conducted at pressures ranging from about 15 psia to about 30 psia.

Aromatics Retention

The catalyst composition should be treated to minimize the loss of aromatics, without substantially inhibiting olefin saturation which prevents formation of the desirable products.

Aromatics loss over the treated catalyst composition of this invention is substantially lower than the aromatics loss sustained over the untreated catalyst.

The activity of the catalyst composition for aromatics ring loss relative to the entire amount of aromatics in the feed, is an effective way to evaluate the aromatics hydrogenation activity of the catalyst. Ideally, aromatics ring loss is less than 1 mole %. However, ring losses of less than 10 mole %, specifically, less than 5 mole %, even more specifically, less than 2 mole %, are acceptable, based on the entire amount of aromatics in the feed. Ring loss is determined using gas chromatography by comparing the amount of aromatics in the feed with the amount of aromatics in the product.

Catalyst Treatment to Retain Aromatics

The extent and methods of treatment of the catalyst including the hydrogenation functionality for minimizing loss of aromatics may vary depending upon the catalyst composition and its method of manufacture, e.g. the method of incorporating the hydrogenation functionality.

Catalyst pretreatment ex situ can be used to accomplish the objectives of the invention.

Typically, steam treatment of the catalyst composition is employed as an effective method for mimizing the aromatics hydrogenation activity of the catalyst composition. In the steaming process the catalyst is, usually, contacted with from about 5 to 100% steam at a temperature of at least about 500° F. to about 1200° F. for at least about one hour, specifically about 1 to about 20 hours at a pressure of 100 to 2500 kPa.

Another method for minimizing the aromatics hydrogenation activity of the catalyst composition is by exposing it to a compound containing an element selected from Group VA or VIA of the Periodic Table of the Elements (CAS Version, 1979). The VIA element specifically contemplated is sulfur. A specifically contemplated group VA element is nitrogen.

Effective treatment is accomplished by contacting the catalyst with a source of sulfur at a temperature ranging from about 600° to 900° F. (316° to 480° C.). The source of sulfur can be contacted with the catalyst via a carrier gas, typically, an inert gas such as hydrogen or nitrogen. In this embodiment, the source of sulfur is typically hydrogen sulfide.

The catalyst composition can also be treated in situ to accomplish the objectives of the invention.

A source of sulfur is contacted with the catalyst composition by adding it to the hydrocarbon feedstream in a concentration ranging from about 50 ppmw sulfur to about 10,000 ppmw sulfur. Any sulfur compound that will decompose to form $H_2S$ and a light hydrocarbon at about 900° F. or less will suffice. Typical examples of appropriate sources of sulfur include carbon disulfide and alkylsulfides such as methylsulfide, dimethylsulfide, dimethyldisulfide, diethylsulfide and dibutyl sulfide. Sulfur treatment can be considered sufficient when sulfur breakthrough occurs; that is, when sulfur appears in the liquid product.

Typically, sulfur treatment is initiated by incorporating a source of sulfur into the feed and continuing sulfur treatment for a few days, typically, up to 10 days, more specifically, from one to five days. The sulfur treatment can be monitored by measuring the concentration of sulfur in the product off gas. During this treatment, the sulfur concentration in the off gas should range from about 20 to about 500 ppmw sulfur, preferably about 30 to 250 ppmw.

Continuously cofeeding a source of sulfur has been found to maintain a sufficiently minimal aromatics hydrogenation activity. The catalyst can be contacted with sulfur during service by cofeeding sulfur to the reactor in varied amounts via the hydrogen stream entering the reactor or the hydrocarbon feedstock. The sulfur can be continuously added to the feedstock throughout the process cycle or the sulfur can be intermittently continuosly added in which this sulfur is cofed continuously for a period of time, discontinued, then cofed again.

Aromatics hydrogenation activity can also be sufficiently minimized by operating the process under conditions of low hydrogen partial pressure. Typically, an appropriately low hydrogen partial pressure is below about 300 psig, ranges from about 100 psia to about 300 psia, specifically about 150 psia to about 250 psia and hydrogen to hydrocarbon mole ratio of less than 3.0, preferably ranging from 1.0 to 2.0. Temperatures, during this phase range from about 700° F. to about 950° F., pressures from about 250 to about 400 psig and W.H.S.V. of about 1.5 to about 4.0. The lower hydrogen to hydrocarbon mole ratios can be used as a catalyst treatment initially upon commencement of the process in order to obtain the desired catalyst performance or it can be used to treat the catalyst after a period of time on stream.

Any one or a combination of these in situ and/or ex situ methods can be employed for minimizing the aromatics hydrogenation activity of the catalyst. It has been found that these methods minimize aromatics hydrogenation activity while sustaining sufficient hydrogenation of olefins which avoids rapid catalyst aging.

The Feed

The $C_9+$ aromatics feed used in this process will usually comprise one or more aromatic compounds containing at least 9 carbon atoms such as, e.g. trimethylbenzenes, dimethylbenzenes, and diethylbenzenes, etc. Specific $C_9+$ aromatic compounds include mesitylene (1,3,5-trimethylbenzene), durene (1,2,4,5-tetramethylbenzene), hemimellitene (1,2,4-trimethylbenzene), pseudocumene (1,2,4-trimethylbenzene), 1,2-methylethylbenzene, 1,3-methylethylbenzene, 1,4-methylethylbenzene, propyl-substituted benzenes, butyl-substituted benzenes, isomers of dimethyl-ethylbenzenes, etc.

Suitable sources of the feed include a $C_9+$ fraction of any refinery process which is rich in aromatics. This aromatics fraction contains a substantial proportion of $C_9+$ aromatics, specifically $C_9$ to $C_{12}$ aromatic hydrocarbons, e.g. at least 80 wt. % $C_9+$ aromatics and, usually, at least about 80 wt. %, usually more than about 90 wt. %, of the hydrocarbons will range from $C_9$ to $C_{12}$. Typically such refinery stream will contain as much as if not more than 90 wt. % $C_9+$ aromatics.

Typical refinery fractions which may be useful include catalytic reformate, FCC naphtha or TCC naphtha.

The feedstock employed contains benzene and/or toluene in addition to the $C_9+$ compounds. The feed can also contain xylenes. This charge will normally constitute at least about 50%, specifically about 40% to about 90%, more specifically, about 50 to 70% by volume of the entire feed, the balance of the feed is made up by $C_9+$ aromatics.

The process feedstock can also include recycle of unconverted materials such as toluene, benzene and $C_9+$ aromatics. The amount of the recycle will, usually, cause the reactor feed composition to vary.

Normally, there are no ethylbenzenes in the feed; however, if there is a significant concentration of ethylbenzenes in the feed, a net conversion would be seen.

Hydrocarbon Conversion Process

The process can be conducted in any appropriate reactor including a radial flow, fixed bed, continuous down flow or fluid bed reactor.

In carrying out the process of this invention, the feed is heated to a temperature within the range of about 600° F. to about 1100° F. at a pressure within the range of from about atmospheric to about 1000 psig. Preferred inlet temperatures for the process of the present invention fall within the range of from about 650° F. to about 1000° F. and total system pressures range from about 50 psig to about 1000 psig, catalyst inventory of about 0.5 to about 4.0 WHSV. In one embodiment of the invention, the process is initiated with a relatively low hydrogen partial pressure; thereafter, the hydrogen concentration is increased, usually gradually, to achieve a hydrogen partial pressure of at least about 200 psia, typically about 220 psia to 250 psia. The hydrogen to hydrocarbon mole ratio is elevated from about 1.5 to about 10, preferably from about 2 to about 6.

The process conditions are maintained to achieve transalkylation and light olefins saturation.

Figure 1:
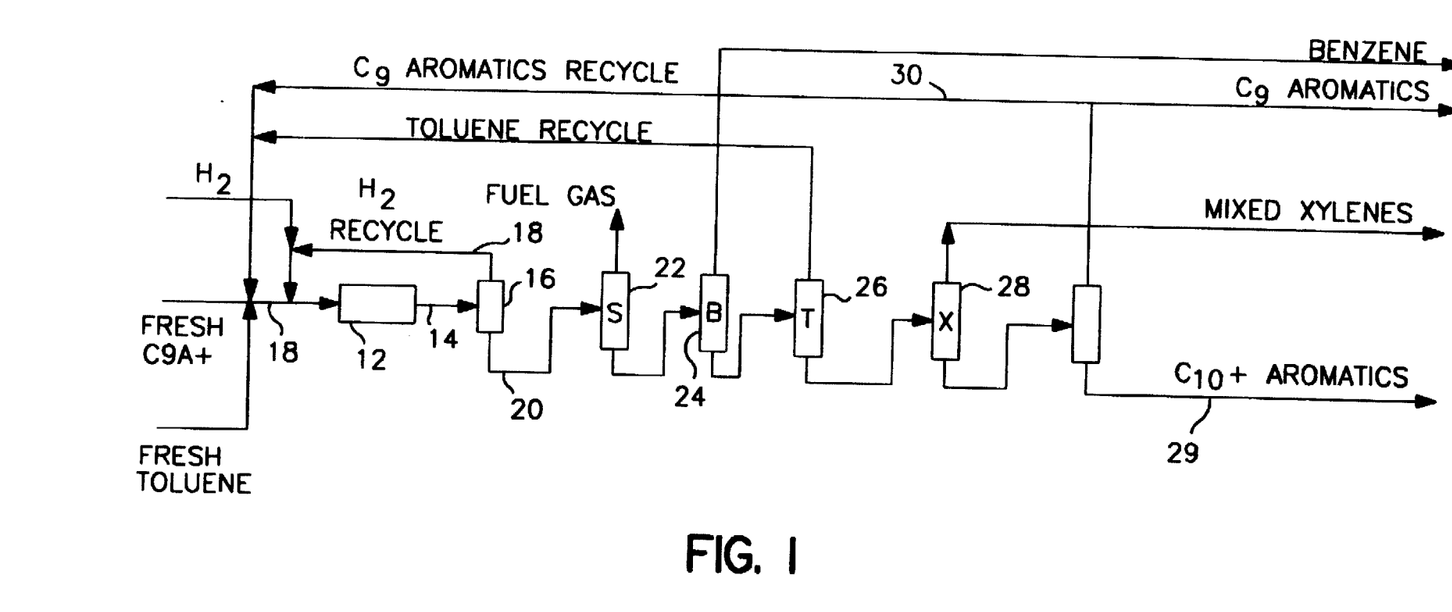
FIG. 1 is a simplified schematic flow diagram of one embodiment of the process of this invention.

Referring to FIG. 1, a simplified process flow diagram is illustrated. The $C_9+$ aromatics stream along with toluene and hydrogen are introduced via line 10 to reactor 12 which contains the transalkylation catalyst of this invention. The reactor is maintained under conditions sufficient so that benzene and methyl aromatics (toluene, xylenes, trimethylbenzenes and tetramethylbenzenes) approach thermodynamic equilibrium through transalkylation reactions. The $C_8$ to $C_{11}$ aromatics having $C_2+$ alkyl groups undergo dealkylation to form light gas and benzene, ethylbenzene and methylbenzenes which can undergo transalkylation reactions. The conditions are maintained to promote the secondary reactions which involve hydrogenation of light olefins which reduce coke. The conditions are also maintained to prevent olefins from taking part in formation of heavy aromatics compounds that can deactivate the catalyst or produce undesirable by-products. These results are achieved without producing a high yield of saturated aromatics. The product of reactor 12 is withdrawn via line 14 and introduced to hydrogen separator 16 which separates hydrogen for recycle to reactor 12 via line 18. The product then passes via line 20 to a stabilizer section 22 which removes $C_5$-fuel gas by known techniques. Thereafter, the product is fractionated into benzene, toluene and xylenes streams in fractionators 24, 26 and 28, respectively, for separation of these streams. The remaining product which comprises unreacted $C_9+$ feed and any heavy aromatics is separated into a $C_9$ aromatics stream 30 and a $C_{10}+$ aromatics stream 29. Stream 30 is recycled back to the reactor feed, removed from the process, or a combination of both (partial recycle). The $C_{10}+$ aromatics stream 29 is suitable for gasoline blending or other product such as solvents.

EXAMPLES

The following examples demonstrate catalyst preparation and pretreatment and performance of the catalyst in the conversion of heavy aromatics and benzene and/or toluene to xylenes.

Example 1

This example demonstrates formation of a platinum exchanged alumina bound ZSM-12 catalyst.

65 parts of ZSM-12 synthesized according to U.S. Pat. No. 3,832,449 was mixed with 35 parts of LaRoche Versal 250 alumina on a dry basis. The mixture was dry mulled and formed into 1/16" cylindrical extrudates. The extrudates were dried, activated and calcined. Platinum (0.1 wt. %) was exchanged into the extrudates using $[(NH_3)_4Pt]Cl_2$. The extrudates were washed, dried and calcined at 660° F. The platinum containing calcined extrudates were steamed at 900° F. for 4 hours. The resulting catalyst was designated as catalyst A.

The finished catalyst had an alpha activity of 53, a surface area of 281 m²/g.

Figure 2:
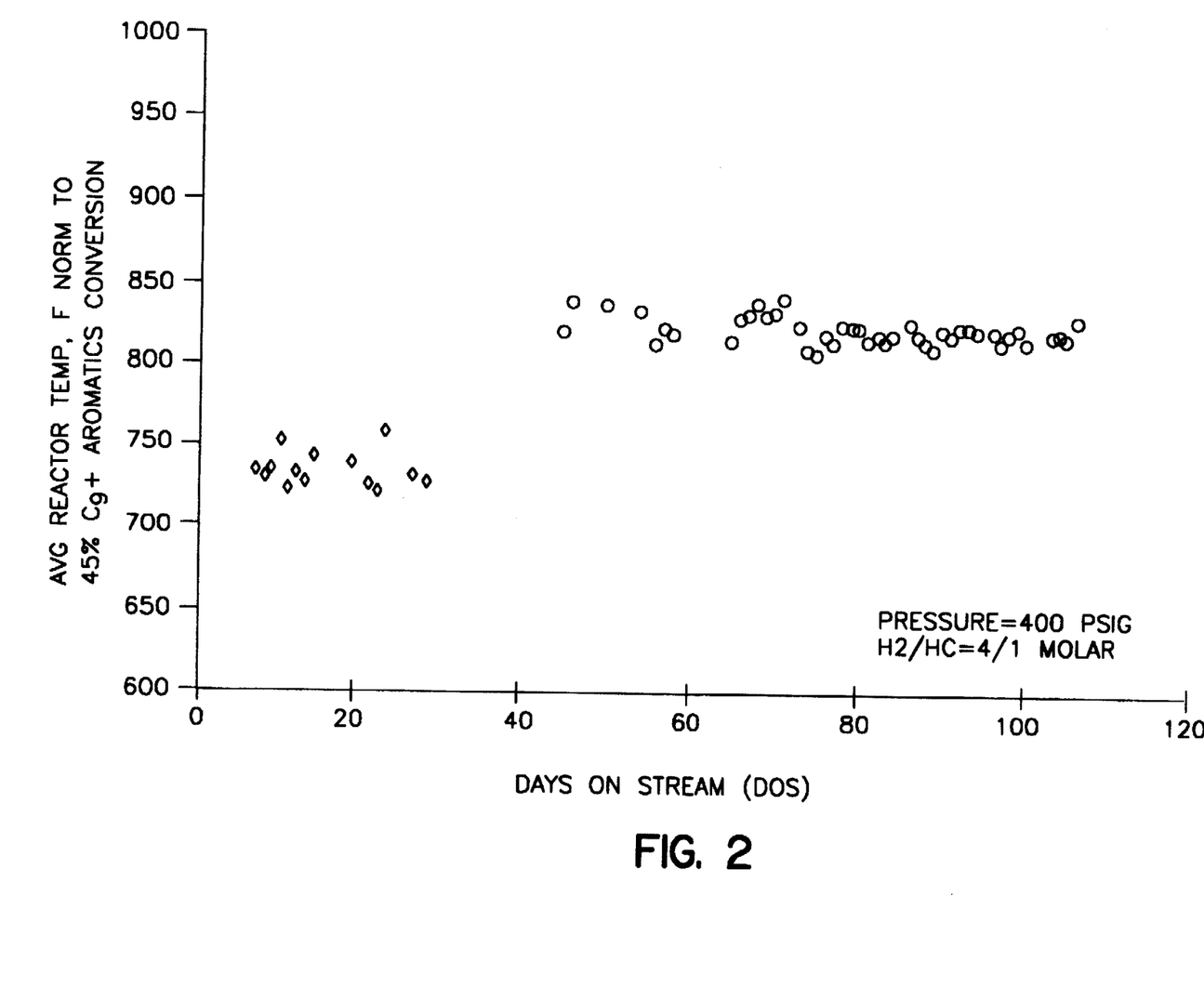
FIG. 2 is a plot of hydrocarbon conversion at constant pressure and hydrogen to hydrocarbon mole ratio at a temperature of about 725° F. and a temperature of about 850° F. as a function of days on stream vs. average reactor temperature.

FIG. 2 is a plot of average reactor temperature vs. days on stream which compared the performance of sulfided catalyst A at a temperature of about 725° F. and a temperature of about 850° F. at constant pressure of 400 psig and hydrogen to hydrocarbon mole ratio of 4:1. The plot shows that the catalyst remained stable at both temperatures within a period from about 10 to 100 days. Elevating the temperature to 850° F. after 40 days achieved a greater $C_9+$ conversion which remained relatively constant for up to 55 days longer.

Example 2

This example demonstrates formation of a platinum containing alumina bound ZSM-12 catalyst.

65 parts of ZSM-12 (dry basis) synthesized according to U.S. Pat. No. 3,832,449 was mixed with 35 parts of LaRoche Versal 250 alumina (dry basis) and with a platinum-containing solution using $[(NH_3)_4Pt]Cl_2$. The amount of platinum used gave a nominal loading of 0.1 wt. % (dry basis). The mixture was dry mull and formed into 1/16" cyclindrical extrudates. The extrudates were dried, activated and calcined. The platinum containing calcined extrudates were steamed at 900° F. for 4 hours. The platinum loading of the finished catalyst was 0.09 wt. %. The resulting catalyst was designated as catalyst B. The finished catalyst had an alpha activity of 77, a surface area of 280 m²/g.

Figure 3:
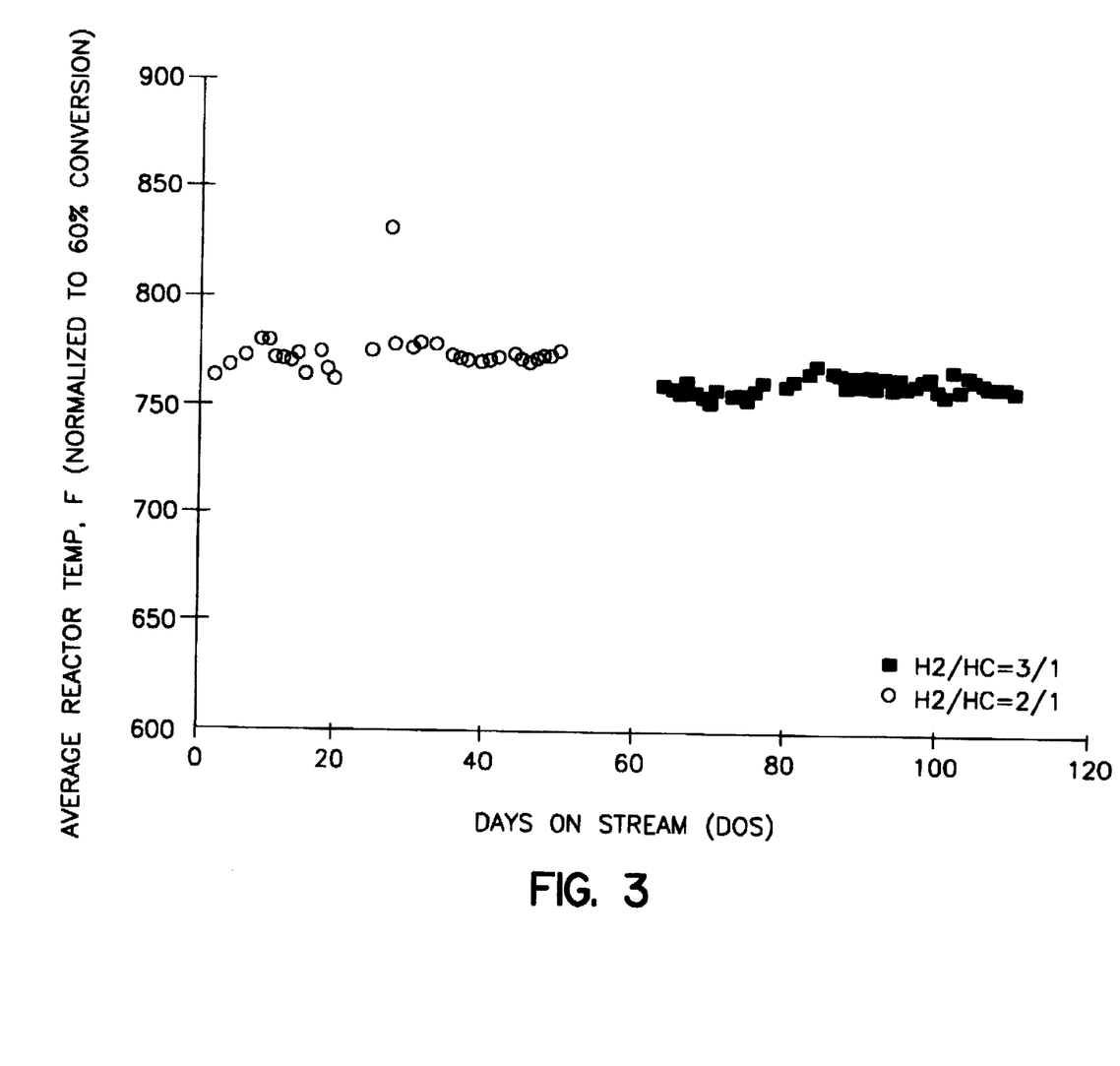
FIG. 3 is a plot of hydrocarbon conversions at constant temperature and pressure at a hydrogen to hydrocarbon mole ratio of 2:1 and 3:1 as a function of days on stream vs. average reactor temperature.

FIG. 3 is a plot of average reactor temperature vs. days on stream which compares the performance of catalyst B at a low hydrogen to hydrocarbon mole ratio (2:1) with the performance of the same catalyst at a higher hydrogen to hydrocarbon mole ratio (3:1). Catalyst B was steamed and sulfided by exposing the catalyst to $H_2S$ in a concentration ranging from between 0.05 and 4.0 wt. % in flowing hydrogen, as carrier, at temperatures ranging from about 650° F. and 800° F. until $H_2S$ was detected in the product gas at a level of approximately 250 ppmw. The plot shows that catalyst performance is relatively stable over a period of over 100 days on stream at a relatively constant temperature of about 750° F. to about 775° F. This plot demonstrates how a low hydrogen to hydrocarbon mole ratio during the start-up phase of the conversion enhances catalyst stability.

Examples 3–4

These examples compare the performance of catalyst A which was steamed after addition of the metal (Example 3) with a catalyst made in accordance with Example 22 of U.S. Pat. No. 5,030,787 which was steamed prior to incorporation of the metal (Example 4) in transalkylating $C_9+$ aromatics and toluene. The results are reported in Table 1.

TABLE 1

| Conversion of $C_9+$ Aromatics and Toluene Over Steamed Catalysts | | |
|---|---|---|
| Reaction Conditions | Example 3 | Example 4 |
| Hydrogenation metal | Steamed | Unsteamed |
| Pressure (psig) | 300 | 250 |
| Temperature (°F.) | 800 | 800 |
| WHSV (hr⁻¹) | 2.5 | 2.6 |
| $H_2$:Hydrocarbon mole ratio | 1/1 | 1/1 |

| Composition (wt. %) | Feed | Product | Feed | Product |
|---|---|---|---|---|
| $C_6$–$C_8$ Aromatics | 48.5 | 70.1 | 62.7 | 77.4 |
| $C_9$ aromatics | 43.0 | 20.5 | 30.4 | 11.0 |
| $C_{10}$ aromatics | 7.8 | 4.3 | 4.8 | 3.1 |
| Aromatic Ring Retention mol. % (loss) | — | 98.9 (1.1) | — | 96.7 (3.3) |

The data reported in Table 1 show that ring retention is significantly better when the hydrogenation metal is steamed as in Example 3. Additionally, the steamed hydrogenation functionality of Example 3 enabled a lower $C_6$ to $C_8$ aromatics feed to be converted to a product containing an amount of $C_6$ to $C_8$ aromatics which was comparable to the amount of $C_6$ to $C_8$ aromatics produced over the higher aromatics feed of Example 4. Moreover, although not reported in the Table of the $C_6$ to $C_8$ aromatics produced in Example 3, 36.0 wt. % were xylenes. In contrast, of the $C_6$ to $C_8$ aromatics produced in Example 4, only 28.6 wt. % were xylenes.

Examples 5–6

These examples demonstrate the advantage of sulfiding catalyst A prior to introduction of the feed and also compare the performance of the presulfided catalyst with a pre-sulfided catalyst which is further treated by adding sulfur to the feed. In both examples catalyst A was employed and the conditions of reaction included a temperature of 800° F., pressure of 400 psig, WHSV of 2.5 and hydrogen to hydrocarbon mole ratio of 4. In Example 5, sulfiding was accomplished by contacting the steamed platinum exchanged ZSM-12 catalyst with about 50 cc/minute of 2% $H_2S$ in hydrogen gas for about 40 minutes at 660° F. to 750° F. In Example 6, the catalyst was further sulfided in situ by cofeeding 600 ppm sulfur (in the form of dibutyl sulfide) with the hydrocarbon feed for two hours. The results of conversion over these sulfided catalysts are shown below in Table 2.

TABLE 2

| Conversion of $C_9+$ Aromatics and Toluene Over Steamed and Sulfur Treated Catalyst A | | |
|---|---|---|
| Product, wt. % of Feed | Feed | Example 5 | Example 6 |
| $C_5-$ | 0 | 36.7 | 26.2 |
| $C_6+$, non-aromatics | 0.4 | 1.3 | 1.0 |
| Benzene | 0 | 4.4 | 6.4 |
| Toluene | 56.0 | 19.1 | 24.0 |

TABLE 2-continued

Conversion of C$_9$+ Aromatics and Toluene Over Steamed and Sulfur Treated Catalyst A

| Product, wt. % of Feed | Feed | Example 5 | Example 6 |
|---|---|---|---|
| Ethylbenzenes | 0.1 | 0.8 | 1.0 |
| Xylenes | 1.8 | 25.2 | 28.0 |
| C$_9$+ Aromatics | 41.7 | 16.2 | 16.0 |
| Aromatic Ring Retention, wt. % (loss) | | 66.0 (44.0) | 75.0 (25.0) |

As the data in Table 2 show there are significant advantages, particularly in the aromatic ring retention and xylenes production, to cofeeding sulfur.

Examples 7-11

These examples demonstrate that a lower aromatics saturation activity of the hydrogenation functionality can be established by operating the process at a low hydrogen to hydrocarbon mole ratio. In these examples, Catalyst A was employed in the transalkylation of a C$_9$+ aromatic hydrocarbon feedstream and toluene. The catalyst was not exposed to sulfur treatment.

TABLE 3

Conversion of C$_9$+ Aromatics and Toluene Under Different Hydrogen:Hydrocarbon Mole Ratios

| Reaction Conditions | Example 7 | Example 8 |
|---|---|---|
| Pressure, psig | 400 | 400 |
| Ave. Temperature, °F. | 780 | 811 |
| Time On Stream, days | 3.1 | 6 |
| Space Velocity, WHSV | 2.4 | 2.4 |
| H$_2$ to hydrocarbon mole ratio | 2:1 | 1:1 |

| Product, Wt. % of Feed | Feed | Product | Product |
|---|---|---|---|
| C$_5$- | — | 13.9 | 4.0 |
| C$_6$+ non-aromatic | 0.1 | 1.0 | 0.1 |
| Benzene | — | 7.7 | 10.8 |
| Toluene | 57.0 | 29.0 | 34.8 |
| Ethylbenzene | 0.1 | 1.8 | 1.5 |
| Xylenes | 1.7 | 26.0 | 28.6 |
| C$_9$+ Aromatics | 41.1 | 22.0 | 20.4 |
| Aromatic Ring Retention, mol % (loss) | | 87.1 (12.9) | 98.7 (1.3) |

The following Table 4 demonstrates that not only did the lower hydrogen to hydrocarbon mole ratio reduce aromatics ring loss, but the ring retention was maintained when the hydrogen to hydrocarbon mole ratio was increased to 4:1. The feed was similar to the feed used in Table 3. In these Examples, the catalyst was treated by steaming and exposure to sulfur.

TABLE 4

Conversion of C$_9$+ Aromatics and Toluene Under Different Hydrogen:Hydrocarbon Mole Ratios

| Reaction Conditions | Example 9 | Example 10 | Example 11 |
|---|---|---|---|
| Pressure, psig | 400 | 420 | 400 |
| Ave. Temperature, °F. | 800 | 800 | 800 |
| Time On Stream, hours | 85.5 | 110 | 230 |
| Space Velocity, WHSV | 4 | 4 | 4 |
| H$_2$ to hydrocarbon mole ratio | 4:1 | 2:1 | 4:1 |
| Aromatic Ring Retention, mol % (loss) | 77.3 (22.7) | 87.5 (12.5) | 90.9 (9.1) |

Examples 12-14

These examples demonstrate continuously cofeeding sulfur to treat the catalyst in situ.

In these examples a Pt/ZSM-12 catalyst was presulfided with about 50 cc/min 2% H$_2$S/H$_2$ for about 40 minutes at 660° F.–750° F. In each example the reaction was operated at a temperature of 800° F., pressure of 300 psig, W.H.S.V. of 2.5 and hydrogen to hydrocarbon mole ratio of 2. After about 125 hours on stream 100 ppmw sulfur was added to the feed and the sulfur was continuously cofed through about 170 hours on stream, at which time the sulfur feed was discontinued to evaluate the effect that continuous addition of sulfur had on the product. Product samples were analyzed at 134 hours on stream (Example 12) at 158 hours on stream (Example 13) and at 206 hours on stream (Example 14). The following Table 5 reports the results of product analysis.

TABLE 5

Continuous Sulfur Addition

| | Example 12 | Example 13 | Example 14 |
|---|---|---|---|
| Sulfur Cofeed | Yes | Yes | No |
| Time on Stream, hours | 134 | 158 | 206 |

| Product, wt. % of Feed | Feed | Product | Product | Product |
|---|---|---|---|---|
| C$_5$- | 0 | 6.1 | 6.0 | 7.3 |
| C$_6$+ Non aromatics | 0 | 0 | 0 | 0.1 |
| C$_6$-C$_8$ Aromatics | 58.0 | 78.1 | 78.0 | 76.6 |
| C$_9$+ Aromatics | 42.1 | 16.1 | 16.6 | 16.4 |
| Ring Retention, mol. % (loss) | — | 97.6 (2.4) | 97.9 (2.1) | 96.1 (3.9) |

The data reported in Table 5 demonstrate the advantages of continuously cofeeding sulfur. Comparing the C$_6$ to C$_8$ aromatics of Example 14 with Examples 12 and 13, it is apparent that continuously cofeeding sulfur maintained a product of higher C$_6$ to C$_8$ aromatics content. Additionally, in Examples 12 and 13 fewer C$_5$– and C$_6$+ nonaromatics (e.g. methylcyclopentane) formed and fewer aromatics were lost. Furthermore, although not reported in Table 3, the hydrogen consumption was significantly reduced with sulfur cofeed. At 134 hours on stream, with sulfur cofeed, the hydrogen consumption was 222.6 SCF/B (Example 12), at 158 hours on stream, with sulfur cofeed, the hydrogen consumption was 202.1 SCF/B (Example 13). In Example 14, after the sulfur cofeed was discontinued, the hydrogen consumption was 312.2 SCF/B.

What is claimed is:

1. A process for converting a feedstock comprising C$_9$+ aromatic hydrocarbons to lighter aromatic products comprising the step of:

contacting a feed comprising the C$_9$+ aromatic hydrocarbons, benzene and/or toluene under transalkylation reaction conditions with a catalyst composition comprising a zeolite having a Constraint Index ranging from at least 0.6 to about 3 and a noble metal hydrogenation functionality to produce a product comprising xylenes, wherein the catalyst composition having a hydrogenation functionality is treated by steaming by exposure to water at high temperatures or by contacting the catalyst composition with a source of sulfur.

2. The process of claim 1 in which the steaming step is operated under conditions of contacting the catalyst composition with from about 5 to 100% steam at a temperature of about 500° F. to about 1200° F.

3. The process of claim 1 in which the source of sulfur is hydrogen sulfide.

4. The process of claim 1 in which the catalyst composition is treated by contacting the catalyst composition with a sulfur cofeed.

5. The process of claim 1 in which the catalyst composition is treated by the step of continuously cofeeding a source of sulfur.

6. The process of claim 4 in which the source of sulfur is an alkylsulfide.

7. The process of claim 4 in which the source of sulfur is carbon disulfide, methylsulfide, dimethylsulfide, dimethyldisulfide, diethylsulfide and dibutylsulfide.

8. The process of claim 1 in which the source of sulfur is added in an amount ranging from about 50 ppmw to about 1,000 ppmw.

9. The process of claim 1 which the contacting step is conducted under a hydrogen partial pressure of below 300 psia.

10. The process of claim 1 in which the noble metal is platinum or palladium.

11. The process of claim 1 in which the zeolite is selected from the group consisting of zeolite beta, ZSM-12 and MCM-22.

12. The process of claim 1 in which the benzene and/or toluene represents at least about 40% to about 90% by volume of the total feedstock.

13. The process of claim 1 in which the feed comprises toluene and C$_9$+ aromatic hydrocarbons.

14. The process of claim 1 in which the transalkylation conditions comprise temperatures ranging from about 650° F. to about 1000° F., hydrogen to hydrocarbon mole ratio ranging from about 1.5 to about 10 and pressures ranging from about 50 to about 1000 psig.

15. The process of claim 1 in which the transalkylation conditions comprise a hydrogen to hydrocarbon mole ratio of less than about 3.0.

16. The process of claim 1 in which the transalkylation conditions comprise a hydrogen to hydrocarbon mole ratio of about 1.0 to 2.0.

17. The process of claim 1 in which the catalyst composition is made by either replacing the original cations of the zeolite, at least in part, with a hydrogenation functionality by ion exchange or by mixing the zeolite with the hydrogenation functionality.

18. The process of claim 17 in which the catalyst composition further comprises a binder.

19. A process for converting a feedstock containing benzene and/or toluene and C$_9$+ aromatic hydrocarbons to a product comprising xylenes comprising the steps of:

treating a catalyst composition comprising a zeolite and a noble metal hydrogenation component with steam and/or a source of sulfur, the zeolite having a constraint index ranging from at least 0.6 to 3;

contacting the treated catalyst with the feedstock in the presence of hydrogen under transalkylation reaction conditions to produce a product comprising xylenes and which comprise lower than about 10% less than the amount of aromatics in the feedstock.

20. The process of claim 19 in which the steaming step is operated under conditions of contacting the catalyst composition with from about 5 to 100% steam at a temperature of about 500° F. to about 1200° F.

21. The process of claim 19 in which the source of sulfur is hydrogen sulfide.

22. The process of claim 19 in which the catalyst is treated with sulfur by adding a source of sulfur to the feed.

23. The process of claim 19 in which the catalyst is treated with from about 50 ppmw to about 10,000 ppmw of sulfur.

24. The process of claim 19 in which the source of sulfur is carbon disulfide, methylsulfide, dimethylsulfide, dimethyldisulfide, dimethylsulfide, diethylsulfide and dibutylsulfide.

25. The process of claim 19 which the step of contacting is conducted under a hydrogen partial pressure of below about 300 psia.

26. The process of claim 19 in which the noble metal is platinum, or palladium.

27. The process of claim 19 in which the zeolite is selected from the group consisting of zeolite beta, ZSM-12 and MCM-22.

28. The process of claim 19 in which the catalyst composition treating step comprises contacting the catalyst composition comprising a zeolite and a hydrogenation component with steam and contacting the steamed catalyst composition with a source of sulfur.

29. The process of claim 28 which further comprises the step of cofeeding a source of sulfur.

30. A process for converting a hydrocarbon feedstock comprising at least about 80 wt. % C$_9$+ aromatic hydrocarbons to lighter aromatic products comprising the step of:

contacting a feed comprising the C$_9$+ aromatic hydrocarbons, benzene and/or toluene under transalkylation reaction conditions with a catalyst composition comprising a zeolite having a Constraint Index ranging from at least 0.6 to about 3 and a noble metal hydrogenation functionality is treated by steaming by exposure to water at high temperatures of by contacting the catalyst composition with a source of sulfur to produce a product comprising xylenes, the product also comprising lower than about 10 mole % less than the amount of aromatics in the feed.

31. The process of claim 30 in which the product comprises lower than about 5 mole % less than the amount of aromatics in the feed.

* * * * *